(12) United States Patent
Ichikawa et al.

(10) Patent No.: US 7,878,653 B2
(45) Date of Patent: Feb. 1, 2011

(54) FUNDUS CAMERA

(75) Inventors: Naoki Ichikawa, Okazaki (JP);
Makihiro Ishikawa, Okazaki (JP)

(73) Assignee: Nidek Co., Ltd., Gamagori-shi (JP)

( * ) Notice: Subject to any disclaimer, the term of this patent is extended or adjusted under 35 U.S.C. 154(b) by 267 days.

(21) Appl. No.: 12/289,961

(22) Filed: Nov. 7, 2008

(65) Prior Publication Data
US 2009/0180073 A1 Jul. 16, 2009

(30) Foreign Application Priority Data
Nov. 8, 2007 (JP) .............................. 2007-291377
Mar. 14, 2008 (JP) .............................. 2008-066848

(51) Int. Cl.
*A61B 3/10* (2006.01)
*A61B 3/14* (2006.01)

(52) U.S. Cl. ...................................... 351/210; 351/205

(58) Field of Classification Search ................. 351/200, 351/205, 206, 208, 210, 221, 222, 243
See application file for complete search history.

(56) References Cited

U.S. PATENT DOCUMENTS

| 5,463,430 A | 10/1995 | Isogai et al. |
| 5,706,072 A | 1/1998 | Kawamura |
| 7,331,670 B2 | 2/2008 | Ichikawa |
| 7,364,295 B2 | 4/2008 | Tawada |
| 2005/0162611 A1 | 7/2005 | Miwa |
| 2006/0114412 A1 | 6/2006 | Tawada |
| 2007/0030450 A1 | 2/2007 | Liang et al. |

FOREIGN PATENT DOCUMENTS

| EP | 1 535 566 A1 | 6/2005 |
| JP | A-6-46999 | 2/1994 |
| JP | A-7-88083 | 4/1995 |
| JP | A-10-85188 | 4/1998 |
| JP | A-2005-160549 | 6/2005 |

*Primary Examiner*—Ricky L Mack
*Assistant Examiner*—Brandi N Thomas
(74) *Attorney, Agent, or Firm*—Oliff & Berridge, PLC

(57) ABSTRACT

A fundus camera capable of favorably photographing a fundus of an examinee's eye comprises a fundus photographing optical system comprising a visible light source which emits illumination light onto the fundus, a focusing lens movable in an optical axis direction thereof, and a fundus image pickup element, an optical system comprising a first photodetector, for detecting a focus state of the photographing optical system with respect to the fundus, a blink sensor which comprises a second photodetector and detects a blink of the eye based on a photo-receiving signal from the second photodetector, and a control unit arranged to suspend photographing upon input of a predetermined signal until the blink is detected by the sensor, and control the light source to emit the light when a predetermined period of time has passed since the blink is detected by the sensor in order to execute the photographing.

6 Claims, 13 Drawing Sheets

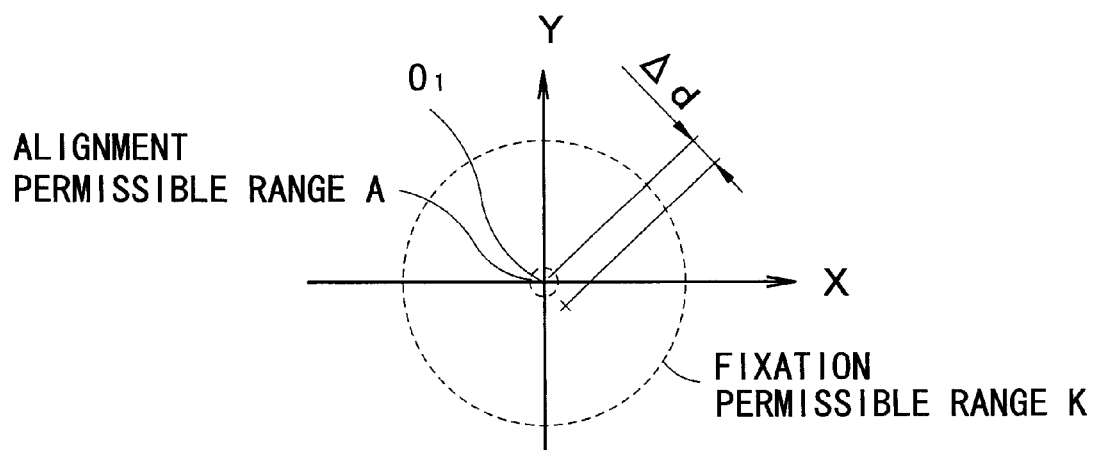
FIG. 8
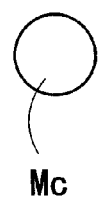
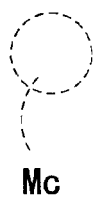
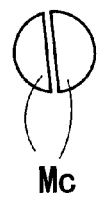
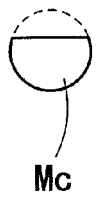
FIG. 9A  FIG. 9B  FIG. 9C  FIG. 9D 17c  17b  17a

PHOTOGRAPHING OPTICAL AXIS

CORNEAL REFLECTION FLARE

PHOTOGRAPHING OPTICAL AXIS

CORNEAL REFLECTION FLARE

CRYSTALLINE LENS REFLECTION FLARE

PHOTOGRAPHING OPTICAL AXIS

CRYSTALLINE LENS REFLECTION FLARE ns of the present invention and, together with the description, serve to explain the objects, advantages and principles of the invention. In the drawings,

FUNDUS CAMERA

BACKGROUND OF THE INVENTION

1. Field of the Invention

The present invention relates to a fundus camera which photographs a fundus of an examinee's eye.

2. Description of Related Art

Conventionally, there is known a fundus camera which photographs a fundus of an examinee's eye. Experience is required for obtaining a favorable fundus image when the fundus of the examinee's eye is photographed by using the fundus camera. There is known a fundus camera in which fundus photographing is automated in order to favorably perform the photographing without requiring experience (see Japanese Patent Application Unexamined Publication No. 2005-160549).

Though the fundus camera of Japanese Patent Application Unexamined Publication No. 2005-160549 makes it easy to perform the photographing without requiring experience by automating the photographing, it is necessary to perform alignment of the apparatus and various condition settings in order to meet photographing conditions, which takes a certain period of time. Therefore, the state of the examinee's eye could be worse than the initial state, e.g., the examinee's eye could be filled with tear, or an opening state of an eyelid of the examinee's eye could be worse at the time of starting the photographing regardless of manual photographing or automatic photographing. It is difficult to obtain a favorable fundus image by performing the photographing in such a state. In addition, it is not possible to obtain a favorable fundus image if the examinee's eye blinks at the time of the photographing.

SUMMARY OF THE INVENTION

An object of the invention is to overcome the problems described above and to provide a fundus camera which is capable of favorably photographing a fundus of an examinee's eye.

To achieve the objects and in accordance with the purpose of the present invention, a fundus camera comprises a photographing optical system for photographing a fundus of an examinee's eye, the photographing optical system comprising a visible light source which emits illumination light onto the fundus, a focusing lens movable in an optical axis direction thereof, and an image pickup element which picks up an image of the fundus, a focus detection optical system comprising a first photodetector, for detecting a focus state of the photographing optical system with respect to the fundus, a blink sensor which comprises a second photodetector and detects a blink of the examinee's eye based on a photo-receiving signal outputted from the second photodetector, and a control unit which is arranged to suspend photographing upon input of a predetermined signal until the blink is detected by the blink sensor, and control the light source to emit the illumination light when a predetermined period of time has passed since the blink is detected by the blink sensor in order to execute the photographing.

Additional objects and advantages of the invention are set forth in the description which follows, are obvious from the description, or may be learned by practicing the invention. The objects and advantages of the invention may be realized and attained by the fundus camera in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 8 is a view for illustrating detection of an alignment deviation amount in the X and Y directions;

FIGS. 9A to 9D are views for illustrating various states of a target image in relation to an eyelid and eyelashes of an examinee's eye;

DETAILED DESCRIPTION OF THE PREFERRED EMBODIMENTS

Figure 1:
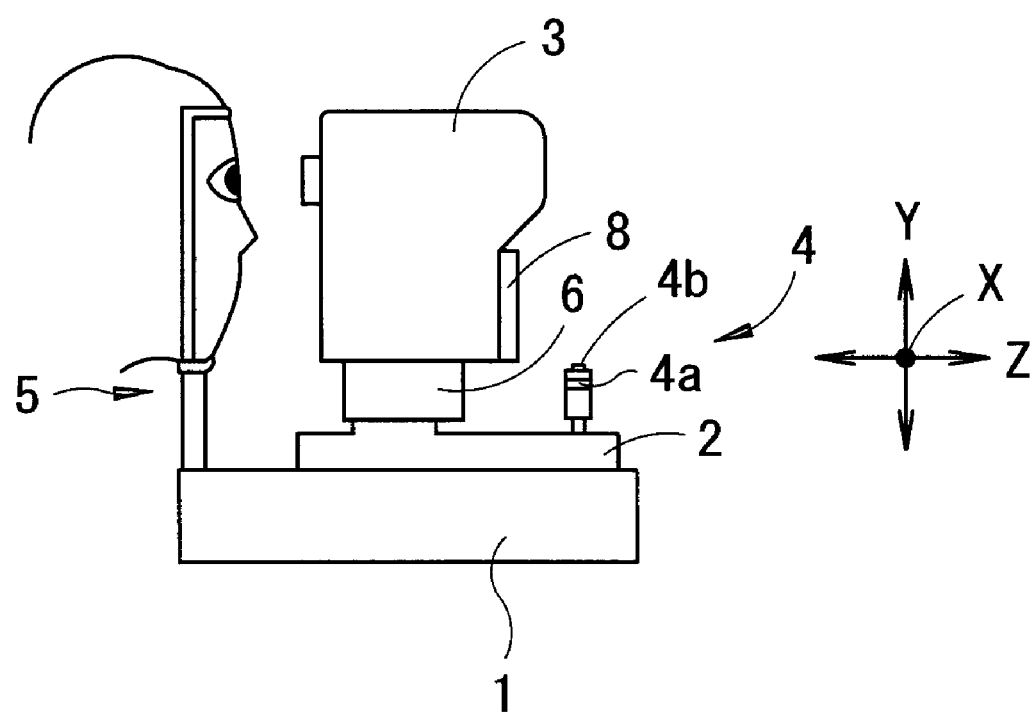
FIG. 1 is a schematic external view of a fundus camera according to a preferred embodiment of the present invention.

A detailed description of one preferred embodiment of a fundus camera embodied by the present invention is provided below with reference to the accompanying drawings. FIG. 1 is a schematic external view of the fundus camera according to the preferred embodiment of the present invention.

The fundus camera comprises a base 1, a mobile base 2 movable in a right/left direction (i.e., an X direction) and a back/forth direction (a working distance direction) (i.e., a Z direction) with reference to the base 1, a photographing unit (an apparatus main body) 3 three-dimensionally movable with reference to the mobile base 2 and housing an optical system to be described later, and a face (head) support unit 5 fixedly placed on the base 1 for supporting a face (a head) of an examinee. The photographing unit 3 is moved in the right/left direction, an up/down direction (i.e., a Y direction) and the back/forth direction with reference to an examinee's eye E by means of an XYZ driving unit 6 provided to the mobile base 2. The mobile base 2 is moved in the X and Z directions on the base 1 through operation of a joystick 4. The photographing unit 3 is moved in the Y direction by means of the XYZ driving unit 6 through rotating operation of a rotation knob 4a. In this case, alignment is performed so that the apparatus main body 3 (a fundus observation/photographing optical system 30) has a predetermined positional relation with respect to the eye E. A monitor 8 which displays a fundus observation image, a fundus photographing image, an anterior-segment observation image and other images is provided on an examiner's side relative to the photographing unit 3.

Figure 2:
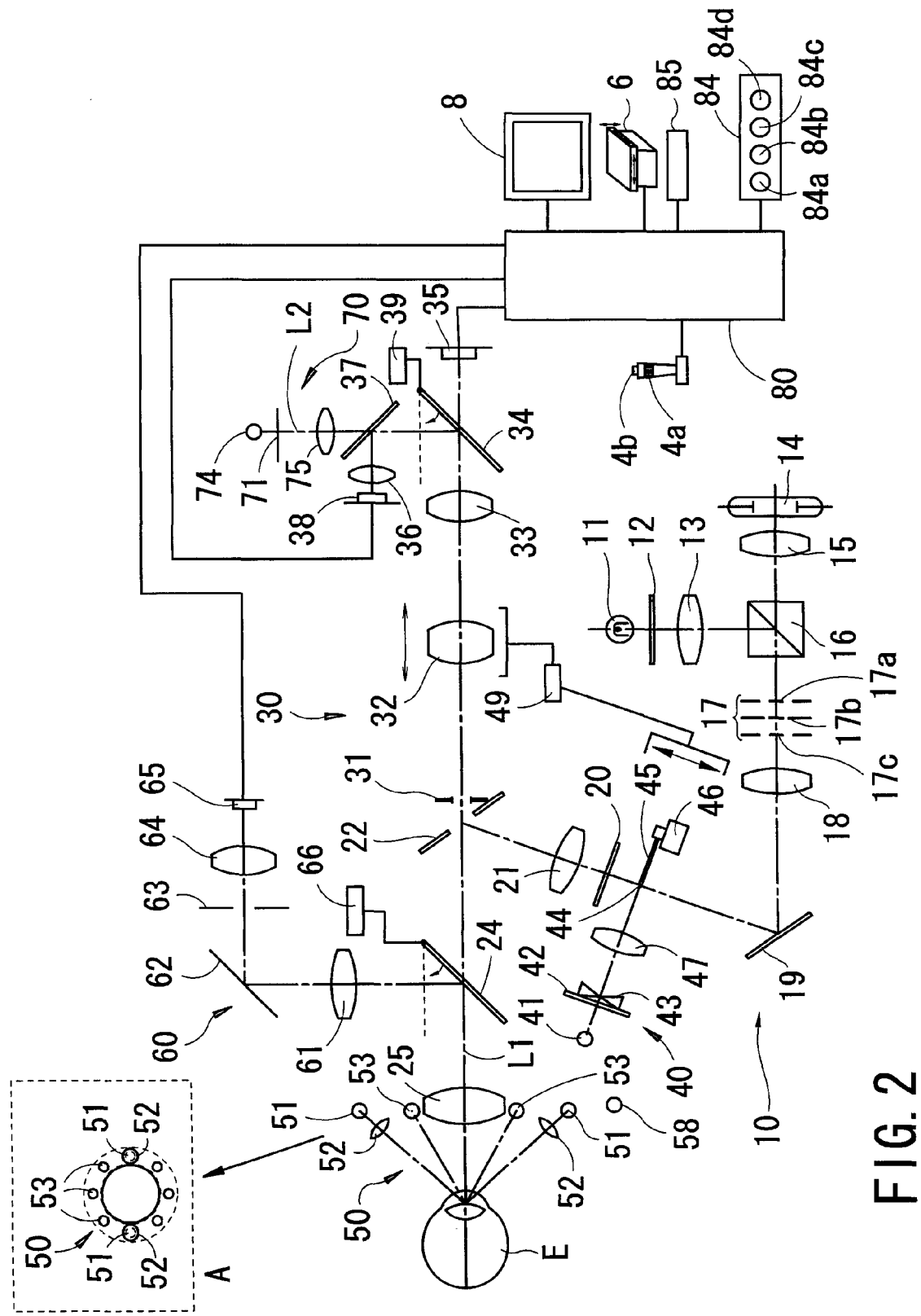
FIG. 2 is a schematic view of an optical system and a control system housed in a photographing unit.

FIG. 2 is a view showing a schematic configuration of the optical system housed in the photographing unit 3 and a control system. The optical system comprises an illumination optical system 10, the fundus observation/photographing optical system 30, a focus target projection optical system 40, an alignment target projection optical system 50, an anterior-segment observation optical system 60, and a fixation target presenting optical system 70.

Illumination Optical System 10

The illumination optical system 10 comprises an observation illumination optical system and a photographing illumination optical system. The photographing illumination optical system comprises a photographing light source 14 such as a flash lamp, a condenser lens 15, a first shielding plate 17a having a circular shielding portion (e.g., a ring slit), a ring slit 17b having a circular shielding portion at the center and a ring-shaped opening, a second shielding plate 17c having a circular shielding portion (e.g., a ring slit), a relay lens 18, a total reflection mirror 19, a black dot plate 20 having a black dot at the center, a relay lens 21, an apertured mirror 22, and an objective lens 25.

The observation illumination optical system comprises a light source 11 for observation such as a halogen lamp, an infrared transmission filter 12 which transmits near infrared light having a wavelength of 750 nm or more, a condenser lens 13, a dichroic mirror 16 placed between the condenser lens 13 and the ring slit 17b, and the first shielding plate 17a through the objective lens 25. The dichroic mirror 16 has properties of reflecting light from the light source 11 and transmitting light from the photographing light source 14.

In the optical systems, when the eye E and the apparatus main body 3 have a positional relation such that the apparatus main body 3 is placed at a predetermined alignment reference position (reference center) with respect to the eye E, the ring slit 17b is placed at a position conjugate with a pupil (an iris) of the eye E, the first shielding plate 17a is placed at a position conjugate with a cornea of the eye E, and the second shielding plate 17c is placed at a position conjugate with a posterior surface of a crystalline lens of the eye E. The first shielding plate 17a, the ring slit 17b, and the second shielding plate 17c in the illumination optical system 10 constitute a shielding member 17. The shielding member 17 functions as flare removing means for preventing corneal reflection light and crystalline lens reflection light formed by fundus photographing light from being included in fundus reflection light and photo-received on a two-dimensional image pickup element 35 for photographing to be described later.

Fundus Observation/Photographing Optical System 30

The fundus observation/photographing optical system 30 for photographing images of a fundus of the eye E comprises a fundus observation optical system and a photographing optical system. The fundus observation/photographing optical system 30 comprises the objective lens 25, a photographing diaphragm 31 arranged in the vicinity of an aperture of the apertured mirror 22, a focusing lens 32 movable in the direction of a photographing optical axis L1, an image forming lens 33, and a pop-up mirror 34 which is insertable into and removable from an optical path by means of an inserting/removing mechanism 39. The photographing optical system and the fundus observation optical system share the objective lens 25 and the photographing diaphragm 31 through the image forming lens 33. The photographing diaphragm 31 is placed at a position substantially conjugate with the pupil with reference to the objective lens 25. The focusing lens 32 is moved in the direction of the optical axis L1 by means of a moving mechanism 49 having a motor. The image pickup element 35 has sensitivity to a visible wavelength range. On the optical path in a reflecting direction of the pop-up mirror 34, a dichroic mirror 37 having properties of reflecting substantially all light within an infrared wavelength range and transmitting substantially all light within a visible wavelength range, a relay lens 36, and a two-dimensional image pickup element 38 having sensitivity to the infrared wavelength range are placed.

A dichroic mirror (a wavelength selecting mirror) 24 functions as an optical path dividing member and is insertable into and removable from the optical path. The dichroic mirror 24 is placed obliquely on an optical path between the objective lens 25 and the apertured mirror 22. The dichroic mirror 24 has properties of reflecting light within an infrared wavelength range of approximately 900 nm or more including light from the alignment target projection optical system 50 and light from an illumination light source 58, and transmitting light within an infrared wavelength range of approximately 900 nm or less including the light from the light source 11. At the time of fundus photographing, the dichroic mirror 24 is flipped up by an inserting/removing mechanism 66 and removed from the optical path. A known mechanism such as a solenoid and a cam may be used for the inserting/removing mechanism 66.

Light emitted from the light source 11 is made into infrared light by the infrared filter 12, passes through the condenser lens 13, and is reflected by the dichroic mirror 16 so as to illuminate the first shielding plate 17a. The light transmitted through the first shielding plate 17a passes through the ring slit 17b, the second shielding plate 17c, the relay lens 18, the mirror 19, the black point plate 20 and the relay lens 21 to reach the apertured mirror 22. The light reflected from the apertured mirror 22 is transmitted through the dichroic mirror 24, and converges once in the vicinity of the pupil and then diffuses to illuminate the fundus.

Figure 5:
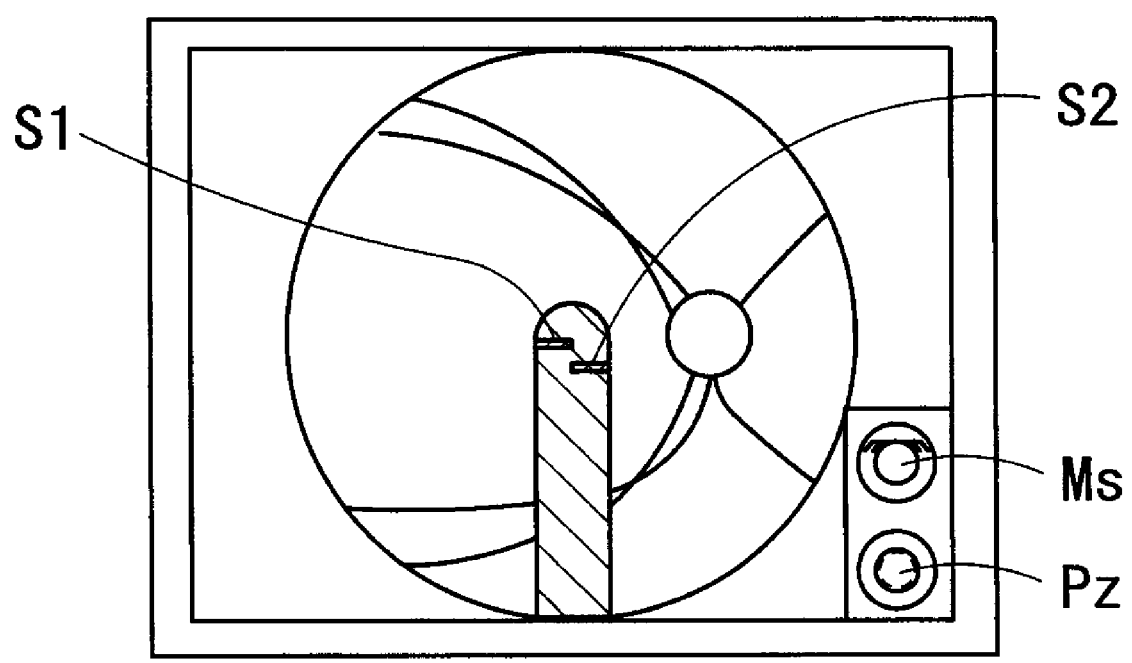
FIG. 5 shows an example of a fundus observation screen.

The light reflected from the fundus passes through the objective lens 25, the dichroic mirror 24, the aperture of the apertured mirror 22, the photographing diaphragm 31, the focusing lens 32, the image forming lens 33, the pop-up mirror 34, the dichroic mirror 37 and the relay lens 36 to form an observation image of the fundus on the image pickup element 38. Output of the image pickup element 38 is inputted to a control unit 80, and the fundus observation image picked up by the image pickup element 38 is displayed on the monitor 8 as shown in FIG. 5.

Visible light emitted from the photographing light source 14 passes through the condenser lens 15 and the dichroic mirror 16, and goes along the same optical path as the illumination light for fundus observation, so that the fundus is illuminated by the visible light. The light reflected from the fundus passes through the objective lens 25, the aperture of the apertured mirror 22, the photographing diaphragm 31, the focusing lens 32 and the image forming lens 33 to form a photographing image of the fundus on the image pickup element 35.

Focus Target Projection Optical System 40

The focus target projection optical system 40 comprises an infrared light source 41, a slit target plate 42, two deflection-angle prisms 43 attached to the slit target plate 42, a projection lens 47, and a spot mirror 44 which is placed obliquely on the optical path of the illumination optical system 10. The spot mirror 44 is fixed to the top end of a lever 45, and is normally placed obliquely on the optical path and is removed from the optical path by rotating a rotary solenoid 46 about the shaft with predetermined timing before the photographing. The spot mirror 44 is placed at a position substantially conjugate with the fundus. The light source 41, the slit target plate 42, the deflection-angle prisms 43, the projection lens 47, the spot mirror 44, and the lever 45 are moved in synchronization with the focusing lens 32 in the direction of an optical axis thereof by the moving mechanism 49. The light having passed through the slit target plate 42 is transmitted through the deflection-angle prisms 43 and the projection lens 47, is reflected by the spot mirror 44, passes through the relay lens 21, the apertured mirror 22, the dichroic mirror 24 and the objected lens 25, and is projected onto the fundus. When the fundus is out of focus, target images S1 and S2 of the slit target plate 42 are separate as shown in FIG. 5, and when the fundus is in focus, the target images S1 and S2 coincide. The target images S1 and S2 projected onto the fundus are picked up by the image pickup element 38 together with the fundus observation image.

Alignment Target Projection Optical System 50

The alignment target projection optical system 50 for projecting target light for the alignment is configured such that a plurality of infrared light sources are concentrically arranged at intervals of 45 degrees having the optical axis L1 at the center as shown in a dashed lined box at the upper left of FIG. 2. To be specific, the alignment target projection optical system 50 comprises first target projection optical systems having infrared light sources 51 and collimating lenses 52 and arranged laterally symmetrical with respect to the optical axis L1 (0 degree and 180 degrees), and second target projection optical systems having six infrared light sources 53 and arranged at positions different from those of the first target projection optical systems. The first projection optical systems project infinite targets onto the cornea from right and left directions, and the second projection optical systems project finite targets onto the cornea from up and down directions or oblique directions. In the main drawing of FIG. 2, the first target projection optical systems (0 degree and 180 degrees) and a part of the second target projection optical systems (45 degrees and 135 degrees) are shown for the sake of illustration.

Anterior-Segment Observation Optical System 60

Figure 3:
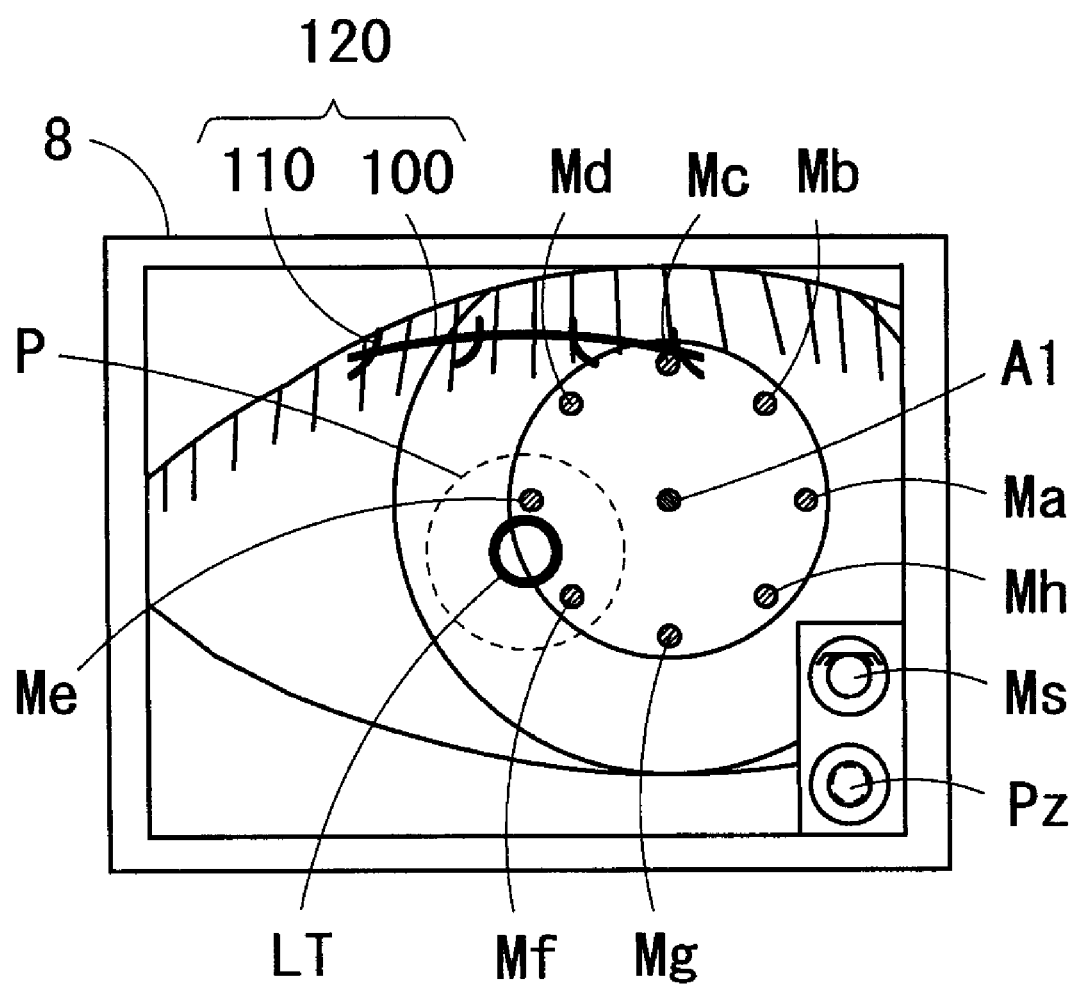
FIG. 3 shows an example of an anterior-segment observation screen when alignment in X and Y directions is not achieved.
Figure 4A:
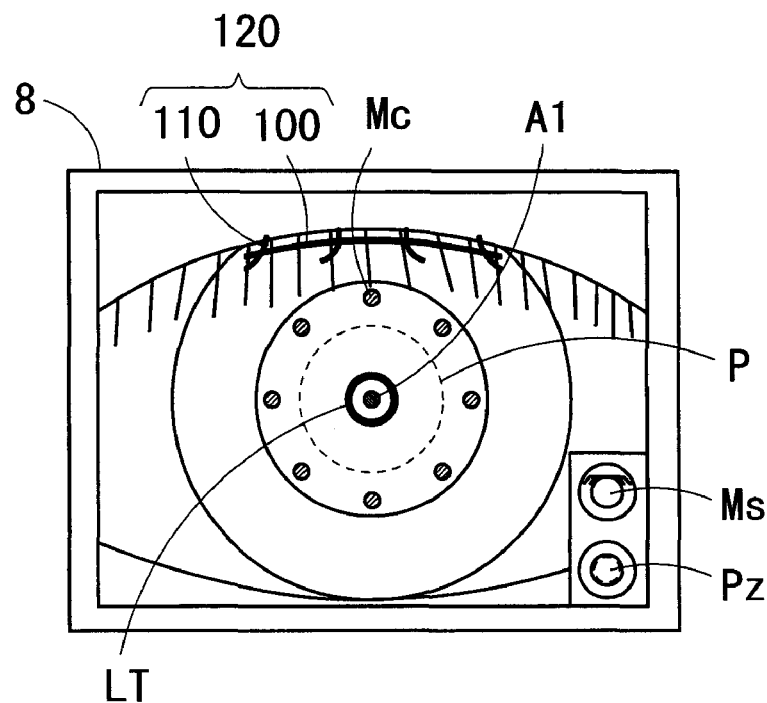
FIGS. 4A and 4B show examples of the anterior-segment observation screen when the alignment in the X and Y directions is achieved.
Figure 4B:
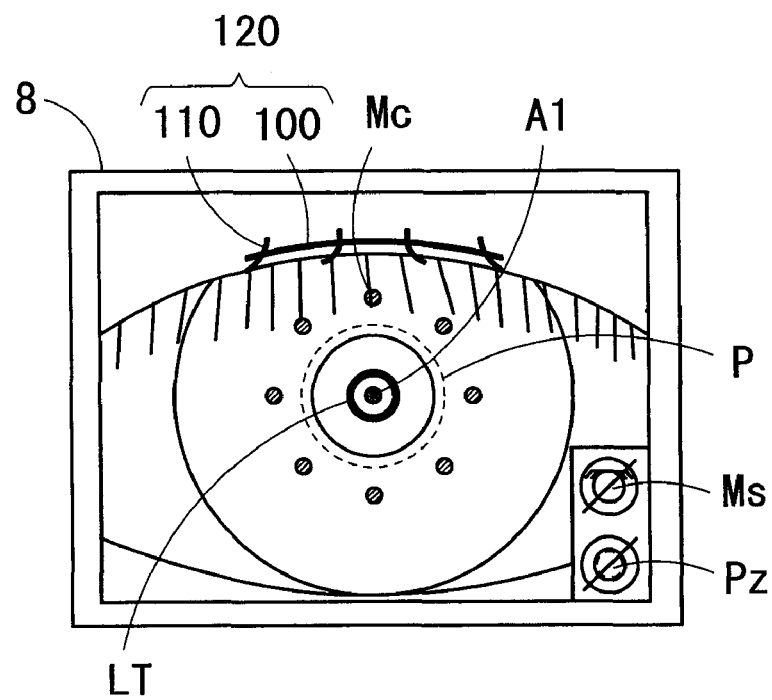

The anterior-segment observation (photographing) optical system 60 for picking up an observation image of an anterior-segment of the eye E comprises a field lens 61, a total reflection mirror 62, a diaphragm 63, a relay lens 64, and a two-dimensional image pickup element (photodetector) 65 having sensitivity to the infrared wavelength range, which are arranged in a reflecting direction of the dichroic mirror 24. The image pickup element 65 doubles as image pickup means for alignment target detection, and picks up the image of the anterior-segment illuminated by the illumination light source 58 and an image of an alignment target. Illumination light emitted from the illumination light source 58 is reflected by the anterior-segment, and the light reflected from the anterior-segment passes through the objective lens 25, the dichroic mirror 24, and the field lens 61 through the relay lens 64, and is photo-received on the image pickup element 65. Alignment target light emitted from the light sources of the alignment target projection optical system 50 is projected onto the cornea, and the light reflected from the cornea is photo-received on (projected onto) the image pickup element 65 via the objective lens 25 through the relay lens 64. Output of the image pickup element 65 is inputted to the control unit 80, and the anterior-segment image picked up by the image pickup element 65 is displayed on the monitor 8 as shown in FIGS. 3 to 4B. The anterior-segment observation optical system 60 doubles as means for detecting an alignment state of the apparatus main body 3 with respect to the eye E. A photo-receiving result obtained by the image pickup element 65 is used for detecting a state of an eyelid and a state of eyelashes of the eye E (details are given later).

Fixation Target Presenting Optical System 70

The fixation target presenting optical system 70 for presenting a fixation target for fixation of the eye E comprises a red light source (a fixation lamp) 74, a shielding plate 71 with an opening, and a relay lens 75, and shares the pop-up mirror 34 through the objective lens 25 with the fundus observation/photographing optical system 30 via the dichroic mirror 37.

The fixation target is formed by illuminating the shielding plate 71 from behind by the light source 74. Illumination light emitted from the light source 74 passes through the opening of the shielding plate 71, the relay lens 75, the dichroic mirror 37, the pop-up mirror 34, the image forming lens 33, the focusing lens 32, the apertured mirror 22, the dichroic mirror 24 and the objective lens 25, and converges at the fundus of the eye E, so that the examinee visually perceives the light from the opening of the shielding plate 71 as the fixation target.

Control System

The image pickup elements 65, 38 and 35 are connected to the control unit 80. The control unit 80 detects the alignment target in the anterior-segment image picked up by the image pickup element 65. The control unit 80 is connected with the monitor 8 and controls the image displayed on the monitor 8. The control unit 8 is connected with the XYZ driving unit 6, the moving mechanism 49, the inserting/removing mechanism 39, the inserting/removing mechanism 66, the rotation knob 4a, a photographing switch 4b, a switch unit 84 having various switches, a memory 85 as storage means, the light sources, and other constituent elements. The control unit 80 detects an alignment deviation amount of the apparatus main body 3 with respect to the eye E based on a photo-receiving signal from the image pickup element 65.

The switch unit 84 preferably comprises a switch 84a for selecting an automatic alignment mode of performing automatic alignment or a manual alignment mode of performing manual alignment, a switch 84b for selecting an automatic focus mode of performing automatic focusing on the fundus or a manual focus mode of performing manual focusing on the fundus, a switch 84c for selecting an automatic photographing mode of automatically executing photographing when photographing conditions are met or a manual photographing mode of executing photographing when the photographing switch 4b is pressed by the examiner, and a focusing switch 84d for performing the manual focusing.

The control unit 80 controls the monitor 8 to electrically form and display a circular reticle mark LT as an alignment reference at a given position on an anterior-segment observation screen shown in FIGS. 3 to 4B (or may display it on a fundus observation screen shown in FIG. 5). In addition, the control unit 80 controls the monitor 8 to electrically form and display an alignment mark A1 on the screen of the monitor 8. A relative distance between the alignment mark A1 and the reticle mark Lt is changed based on the alignment deviation amounts detected by the control unit 80.

Descriptions of operations of the fundus camera having the configuration as described above will be given. The descriptions will be given based on a case where the automatic alignment mode, the automatic focus mode and the automatic photographing mode are selected by using the switches 84a to 84c referring to the flow charts shown in FIGS. 6 and 7.

First, the face of the examinee is supported by the face support unit 5. In the initial stage, the dichroic mirror 24 is inserted into the optical path of the fundus observation/photographing optical system 30, and the anterior-segment image picked up by the image pickup element 65 is displayed on the monitor 8. The examiner performs tilting operation of the joystick 4 and moves the photographing unit 3 in the X and Y directions in order to make the anterior-segment image appear on the monitor 8. When the anterior-segment image subsequently appears on the monitor 8, eight target images Ma to Mh appear as shown in FIG. 3.

When the alignment target image is detected by the image pickup element 65, the control unit 80 starts automatic alignment control. The control unit 80 detects an alignment deviation amount Δd of the apparatus main body 3 with respect to the eye E based on the photo-receiving signal from the image pickup element 65. To be specific, the control unit 80 detects the X and Y coordinates of the center of a ring formed by the target images Ma to Mh as a substantial corneal center. Then, the control unit 80 calculates the alignment deviation amount Δd between an XY alignment reference position O1 which is previously set on the image pickup element 65 (e.g., an intersection of an image pickup surface of the image pickup element 65 and the optical axis L1) and the coordinates of the substantial corneal center (see FIG. 8).

The control unit 80 controls driving of the XYZ driving unit 6 to perform the automatic alignment in order that the alignment deviation amount Δd may fall within an alignment permissible range A for alignment completion. The appropriateness of the alignment state in the X and Y directions is judged based on whether the alignment deviation amount Δd falls within the alignment permissible range A and such a state continues for a certain period of time (e.g., 10 frames of image processing or 0.3 seconds) (i.e., whether an alignment condition A is met).

The control unit 80 obtains an alignment deviation amount in the Z direction by comparing a distance between the target images Ma and Me at an infinite distance and a distance between the target images Mh and Mf at a finite distance. The control unit 80 obtains the alignment deviation amount in the Z direction by utilizing a characteristic that when the apparatus main body 3 deviates in the working distance direction, the distance between the target images Ma and Me hardly changes while the distance between the target images Mh and Mf changes (for details, see U.S. Pat. No. 5,463,430 corresponding to Japanese Patent Application Unexamined Publication No. Hei6-46999).

The control unit 80 obtains the alignment deviation amount in the Z direction with respect to the alignment reference position, and controls the driving of the XYZ driving unit 6 to perform automatic alignment in order that the alignment deviation amount may fall within an alignment permissible range for alignment completion. The control unit 80 judges the appropriateness of the alignment state in the Z direction based on whether the alignment deviation amount in the Z direction stably falls within the alignment permissible range for a certain period of time (i.e., whether an alignment condition is met). According to the preferred embodiment of the present invention, alignment permissible widths in the Z direction are asymmetrical with respect to the alignment reference position. Therefore, it is possible to obtain a fundus photographing image with less flare as much as possible while shortening the time required for the alignment. Detailed descriptions of the alignment permissible widths will be given later.

If the alignment states in the X, Y and Z directions meet alignment completion conditions, the control unit 80 judges that the alignment is achieved and shifts to the next step. However, if the alignment deviation amounts in the X, Y and Z directions become out of the alignment permissible ranges due to movement of the eye E after starting the automatic alignment, the control unit 80 moves the apparatus main body 3 again so that the alignment deviation amounts fall within the alignment permissible ranges. In other words, the automatic alignment control continues until the photographing is executed.

Then, the control unit 80 detects the appropriateness of a pupil diameter (a pupil state) of the eye E. The appropriateness of the pupil diameter is detected based on whether or not an edge of the pupil detected in the anterior-segment image picked up by the image pickup element 65 is out of a predetermined pupil judgment area. The pupil judgment area is set to have a diameter with reference to the image center (the optical axis L1) through which the fundus illumination light can be transmitted (e.g., 4 mm in diameter). As a simple manner, four points on the pupil edge which are detected in the X and Y directions with reference to the image center are used. When the points of the pupil edge are out of the pupil judgment area, illumination intensity at the time of photographing is fully ensured (for details, see Japanese Patent Application Unexamined Publication No. 2005-160549). The judgment of the appropriateness of the pupil diameter continues until photographing is performed, and a result of the judgment is displayed on the monitor 8. The judgment result is indicated by an icon Pz as shown in FIGS. 3 to 5. The icon Pz shown in FIGS. 3, 4A and 5 indicates that the pupil diameter is appropriate, and the icon Pz shown in FIG. 4B indicates that the pupil diameter is not appropriate (error). A diaphragm for a small pupil diameter may be automatically inserted into the optical path instead of a normal diaphragm when the pupil diameter is judged to be insufficient. When the pupil diameter is judged to be appropriate, the control unit 80 shifts to the next step.

Next, the control unit 80 detects the state of the eyelid and the state of the eyelashes (an eyelid opening state) of the eye E based on the photo-receiving signal from the image pickup element 65, and then judges the appropriateness of the state of the eyelid and the state of the eyelashes of the eye E based on a result of the detection. This process is performed for the purpose of preventing the illumination light to be projected onto the fundus from being reflected by the eyelid or the eyelashes, being photo-received on the image pickup element 35, and causing flare in the fundus photographing image.

The following descriptions are given based on a case where the appropriateness of the state of the eyelid and the appropriateness of the state of the eyelashes are judged separately.

In the detection of the state of the eyelid, the control unit 80 judges the appropriateness of the state of the eyelid based on whether or not at least one of the alignment target images formed in the upper portion of the cornea of the eye E (e.g., the target image Mc) is detected by the image pickup element 65 on the precondition that the alignment is achieved. When the alignment target image is not detected (see FIG. 9B), the eyelid opening state is judged to be insufficient. In such a case, the state of the eyelid and the state of the eyelashes of the eye E are judged to be not appropriate (error).

In addition, even if the alignment target image in the upper portion of the cornea (e.g., the target image Mc) is detected in a predetermined area on the image pickup element 65, the control unit 80 analyzes the detected image in detail, detects the state of the eyelashes, and judges the appropriateness of the state of the eyelashes.

For example, when an eyelash falls on the light forming the target image Mc, a part of the light is blocked by the eyelash, and the target image Mc is photo-received on the image pickup element 65 in the state of being split vertically (or obliquely) (i.e., a black vertical line is formed on the target image Mc).

Therefore, the control unit 80 detects whether or not the state of the eyelashes is appropriate for the photographing by judging whether the target image Mc is split substantially horizontally by image processing. When the target image Mc is detected in the state of not being chipped, e.g., in the state of not being vertically split (see FIG. 9A), the control unit 80 judges that both of the state of the eyelid and the state of the eyelashes are appropriate. In addition, when the target image Mc is detected in the state of being vertically split (see FIG. 9C), the control unit 80 judges that the state of the eyelashes is not appropriate (error) while the state of the eyelid is appropriate. For the sake of the simplification, the judgment as described above may be performed based on whether a plurality of bright points the size of which is smaller than the normal size of the target images are formed on a predetermined area on the image pickup element 35. In addition, the state of the eyelashes may be judged based on the presence or absence of the black vertical line on the target image Mc. The judgment of the appropriateness of the state of the eyelid and the state of the eyelashes continues until photographing is performed, and a result of the judgment is displayed on the monitor 8. The judgment result is indicated by an icon Ms as shown in FIGS. 3 to 5. The icon Ms shown in FIGS. 3, 4A and 5 indicates that the eyelid opening state is appropriate, and the icon Ms shown in FIG. 4B indicates that the eyelid opening state is not appropriate (error). The state of the eyelid may be judged to be not appropriate (error) when an upper portion of the target image Mc is chipped as shown in FIG. 9D. When the eyelid opening state is judged to be appropriate, the control unit 80 shifts to the next step.

Next, the control unit 80 performs the automatic focusing on the fundus of the eye E. FIG. 5 shows an example of the fundus observation image picked up by the image pickup element 38, where the target images S1 and S2 of the focus target projection optical system 40 are formed at the center of the fundus observation image. When the fundus is out of focus, the target images S1 and S2 are separate, and when the fundus is in focus, the target images S1 and S2 coincide. The target images S1 and S2 are subjected to detection processing by an image processing unit (not shown), and separation information of the target images S1 and S2 is transferred to the control unit 80. Based on the separation information of the target images S1 and S2, the control unit 80 drives the moving mechanism 39 in order to make the target images S1 and S2 coincide so that the fundus is in focus. When the target images S1 and S2 are not made coincide by the automatic focusing, the control unit 80 may stop the automatic focusing and switch to the manual focusing by the examiner. When the focus state is judged to be appropriate, the control unit 80 shifts to the next step.

FIGS. 4A and 4B show examples of the anterior-segment observation screen to be displayed on the monitor 8 when the automatic alignment, the pupil diameter judgment, the eyelid and eyelash judgment, and the automatic focusing are performed as described above.

At predetermined positions in the center of the screen of the monitor 8, the reticle mark LT and a circular mark P which indicates a smallest photographable pupil diameter are electrically formed and synthetically displayed (superimposed) on the anterior-segment image.

The control unit 80 controls the monitor 8 to display, together with the anterior-segment image, a checking target 120 which gives an indication for the examiner to judge the eyelid opening state at a predetermined position on the screen of the monitor 8. The checking target 120 comprises an eyelid checking target 100 for allowing the examiner to check the state of the eyelid, and eyelash checking targets 110 for allowing the examiner to check the state of the eyelashes. The checking target 120 is electrically displayed at the predetermined position in the upper portion on the screen of the monitor 8. The eyelid opening state is judged by checking whether the eyelid and the eyelashes of the eye E displayed on the screen of the monitor 8 are positioned lower than the target 120 (i.e., the target 120 indicates a permissible lower limit position) on the precondition that the positional relation between the examinee's eye and the apparatus main body 3 falls within the alignment permissible range. The targets 100 and 110 are graphics depicting an eyelid and eyelashes of a human eye. The target 100 is a curved line which extends laterally and is curved upward, and the targets 110 are lines which intersect with the target 100 substantially perpendicularly.

After the automatic alignment is performed, a corneal vertex (or a pupil center) of the eye E is positioned in the vicinity of an alignment reference position (the center of the reticle mark LT) on the screen of the monitor 8. If the eyelid opening state is not appropriate (error), the control unit 80 suspends the automatic control for the subsequent steps, and controls the monitor 8 to display the anterior-segment image and error information. At this time, the examiner can judge the eyelid opening state of the examinee's eye by referring to the targets 100 and 110 on the monitor 8. If the eyelid of the examinee's eye is positioned above the target 100 (see FIG. 4A), the examiner can confirm that the eyelid is positioned above the permissible lower limit position, and if the eyelid of the examinee's eye is positioned below the target 100 (see FIG. 4B), the examiner can confirm that the eyelid is below the permissible lower limit position.

Figure 10:
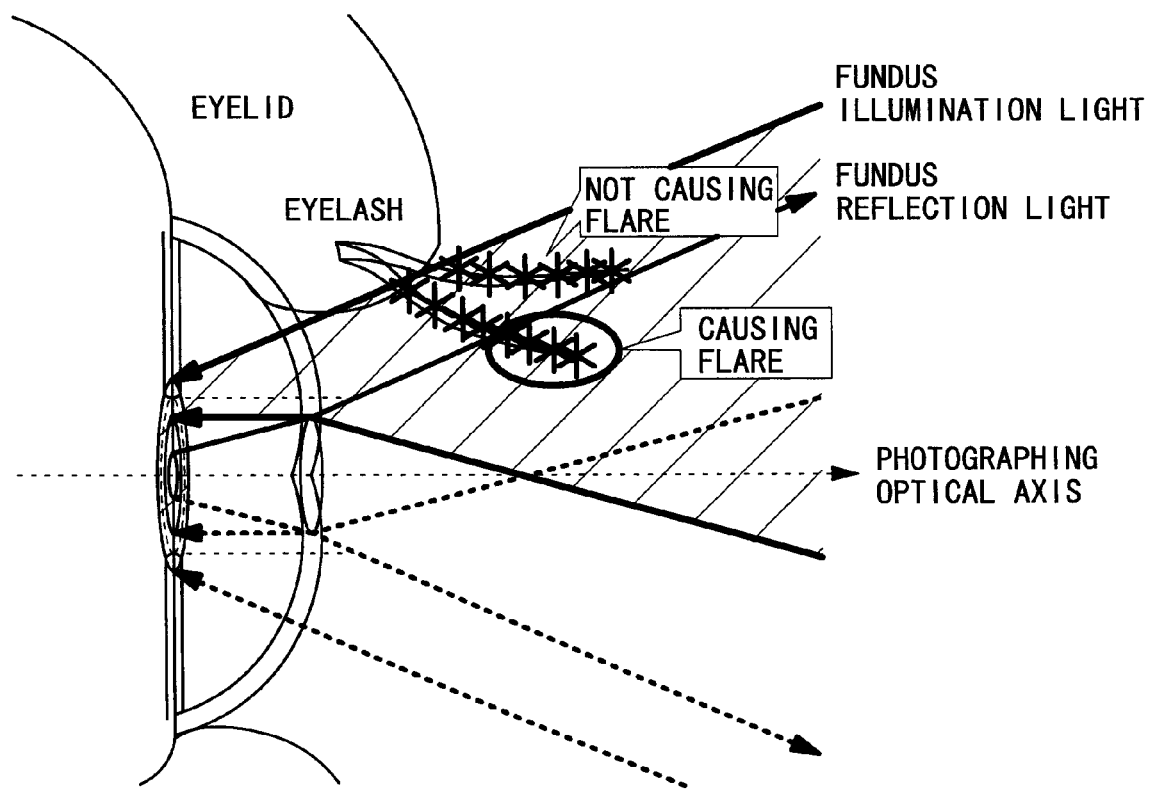
FIG. 10 is a view showing an anterior-segment for illustrating a relation between the eyelashes of the examinee's eye and flare.

The predetermined position at which the target 100 is displayed is set so that the examiner can judge whether the state of the eyelid is appropriate based on a vertical positional relation between the position of the eyelid in an alignment completion state and a display position of the target 100. To be specific, as shown in FIG. 10, in order that the eyelashes extending downward from the eyelid may be prevented from entering a common optical path common to the fundus illumination light and the fundus reflection light, an amount of the downward extension of the eyelashes is taken into consideration, and the permissible lower limit position of the eyelid is set above the position where the eyelid reaches in the common optical path. When the anterior-segment observation screen is displayed on the monitor 8, the control unit 80 controls the monitor 8 to display the target 100 at a display position corresponding to the permissible lower limit position of the eyelid set as described above. If the eyelashes are positioned in the common optical path, the fundus illumination light is unintentionally reflected from the eyelashes and photo-received on the image pickup element 35 as the reflection light, causing flare in the fundus photographing image.

Displaying the targets 100 and 110 allows the examiner to be straightforwardly reminded of the need to check the state of the eyelashes in addition to the state of the eyelid during the judgment of the eyelid opening state. In addition, displaying the target 110 below the target 100 allows the examiner to be straightforwardly reminded of the possibility of the occurrence of an error depending on the state of the eyelashes even if the state of the eyelid is appropriate.

Because the targets 100 and 110 are provided in addition to the icon which indicates the detection result and is displayed on the monitor 8, the examiner can visually judge whether the state of the eyelid and the state of the eyelashes of the examinee's eye are appropriate for the photographing.

When the anterior-segment observation screen is displayed on the monitor 8, the control unit 80 may control the monitor 8 to highlight the target 100 and the targets 110 individually based on the detection results on the state of the eyelid and the state of the eyelashes of the examinee's eye.

To be specific, if both of the state of the eyelid and the state of the eyelashes of the examinee's eye are judged to be not appropriate (error), the control unit 80 controls the monitor 8 to blink the target 100 (or both of the targets 100 and 110) in order to inform the examiner that the eyelid opening state is insufficient.

If the state of the eyelashes is judged to be not appropriate (error) and the state of the eyelid is judged to be appropriate, the control unit 80 controls the monitor 8 to blink the target 110 and informs the examiner that the eyelid opening state is insufficient. In such a case, the examiner makes operations for appropriately performing the photographing on the examinee's eye based the given information (e.g., the examiner instructs the examinee to open the eyes widely, or lifts the eyelid of the examinee's eye) in order that the state of the eyelid and the state of the eyelashes may be judged to be appropriate by the control unit 80.

When highlighting the targets 100 and 110 as described above, it is enough if the control unit 80 can highlight that the state of the eyelashes is not appropriate. For example, the color of the targets 110 is changed, or the lines of the targets 110 are made thick. Alternatively, the control unit 80 may specify the position of the eyelid or the eyelash causing error based on the photo-receiving result obtained by the image pickup element, and control the monitor 8 to display an additional target (preferably, a target depicting an eyelid or an eyelash) at the specified position on the screen of the monitor 8. For example, a straight line or a curved line depicting an eyelash is displayed between the reticle mark LT and the target 100. In such a case, the lowest position of the eyelash is detected by image processing and the color of the straight line or the curved line depicting an eyelash is changed based on a result of the detection.

Figure 7:
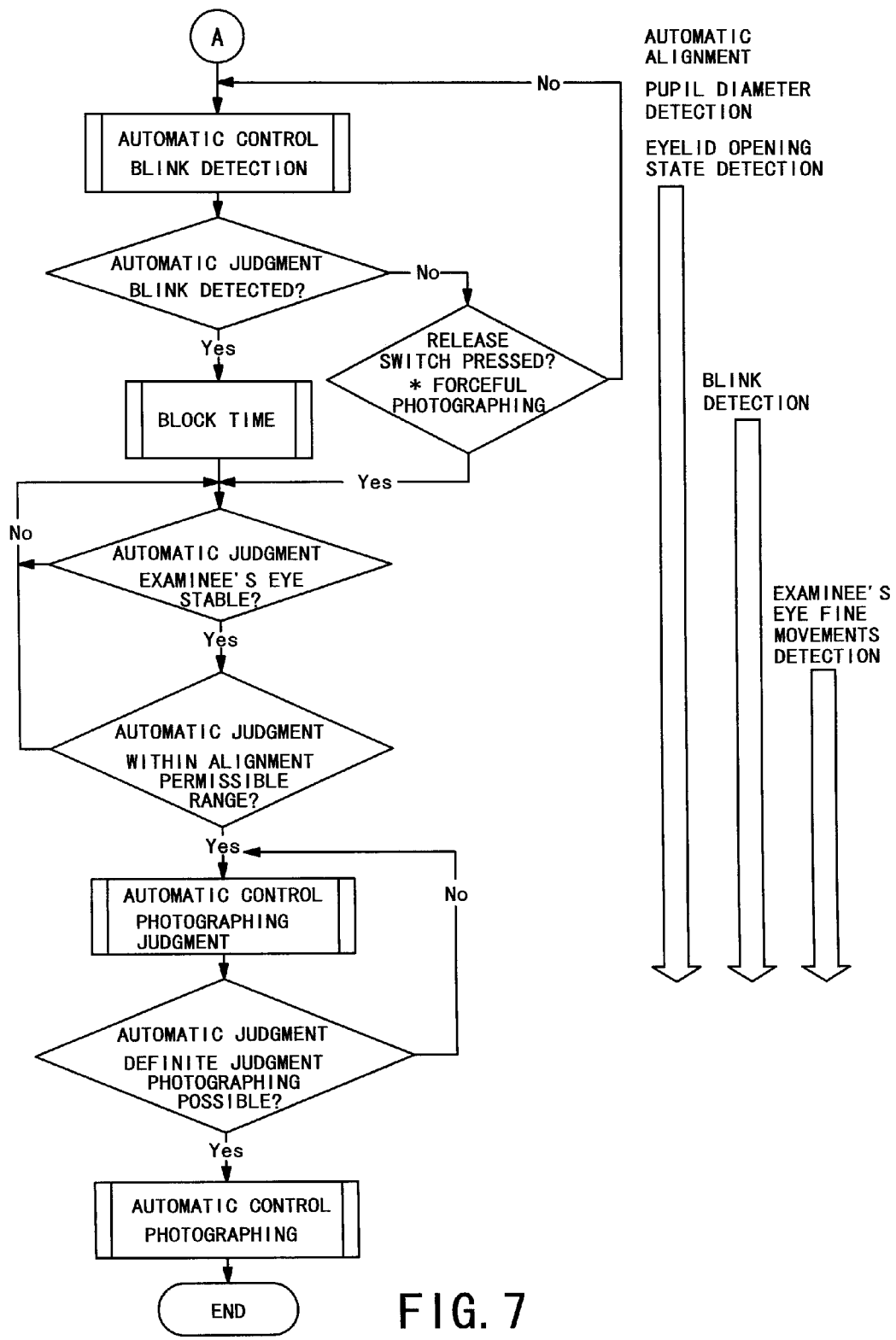
FIG. 7 is a flow chart showing operations of the apparatus.

Descriptions of switching control from the anterior-segment observation screen to the fundus observation screen and operations at the time of automatic photographing will be given (see the flowchart of FIG. 7). When the predetermined alignment conditions are met, the predetermined focus condition is met, and the eyelid opening state and the pupil state are judged to be appropriate, the control unit 80 controls the monitor 8 to switch the image displayed thereon from the anterior-segment image to the fundus observation image. The control unit 80 controls the monitor 8 to clear the target image 120 (the targets 100 and 110) on the screen of the monitor 8 in order that the targets 100 and 110 may be hidden in response to the switching to the fundus observation image display. In addition, the control unit 80 controls the light source 41 to stop lighting and drives the rotary solenoid 46 to remove the spot mirror 44 and the lever 45 from the optical path. By stopping the projection of the focus target before a trigger signal for starting photographing is generated, the examinee is allowed to fixate the fixation lamp without being misled by the visible focus target, which prevents the fixation of the examinee's eye from being disturbed.

When the predetermined conditions as described above are met, the control unit 80 judges that the automatic photographing is in an enabled state. The control unit 80 starts detection of a blink of the examinee's eye, sets the timing of performing the automatic photographing taking the detection of the blink of the examinee's eye as a trigger, and performs the automatic photographing using the set photographing timing. In other words, at least during a period in which the examinee's eye does not blink, the control unit 80 suspends the photographing.

In the detection of the blink, the occurrence of closing and opening movements of the eyelid (movements of the eyelid such that the eyelid closes and opens) from the state of being open is judged based on whether the target image Mc is detected after a predetermined period of time has passed (e.g., 0.5 seconds or less) since the target image Mc is switched from the state of being detected in the predetermined area on the image pickup element 35 to the state of not being detected therein. The condition that the target image is not detected (the eyelid is being closed) for a predetermined period of time (e.g., 0.5 seconds) is set because the closing and opening movements of the eyelid at relatively low speed may spread tear fluid, which has gathered because the eyelid has been open for a long time, over the cornea appropriately for the photographing. When the photographing switch 4b is pressed by the examiner during the detection of the blink, the control unit 80 may skip processes up to judgment of the fixation to be described later (i.e., skip the blink detection) and forcefully shifts to the photographing.

When the blink of the examinee's eye is detected, the control unit 80 suspends the photographing for a predetermined period of time (e.g., 0.5 seconds) from the detection of the blink (see a block period in FIG. 11) and sets the timing of cancelling the suspension of the photographing as the photographing timing. The automatic photographing is performed at the set photographing timing based on a result on the alignment detection, a result on the fixation detection to be described later, and other results. The predetermined period of time during which the photographing is suspended is provided after the detection of the blink because the fixation of the examinee's eye is not stable immediately after the blink and movements of the examinee's eye during the photographing could result in flare in the fundus photographing image.

When the predetermined period of time during which the photographing is suspended has passed, the control unit 80 detects stability of the fixation of the examinee's eye after the detection of the blink (i.e., detect fine movements of the examinee's eye). To be specific, whether or not the fixation is stable is judged based on whether or not the alignment deviation amount falls within a fixation permissible range K, which is wider than the alignment permissible range A, for a predetermined period of time ΔT2 (e.g., 1 second) without interruption in a predetermined period of time ΔT1 (e.g., 2 seconds) after the detection of the blink. Starting the photographing when the stability of the fixation is detected after the detection of the blink makes it possible to prevent flare from being caused in the fundus photographing image due to the movement of the examinee's eye during the photographing and to smoothly start the photographing after the detection of the blink.

When the alignment deviation amount is detected to fall within the fixation permissible range K for the predetermined period of time ΔT2 without interruption in the predetermined period of time ΔT1 after the detection of the blink, the control unit 80 judges that the fixation is stable. Then, the control unit 80 definitely judges the appropriateness of the alignment conditions, the state of the eyelid, the state of the eyelashes and the pupil diameter, and generates the trigger signal for starting photographing if they are judged to be appropriate. In other words, the control unit 80 performs the automatic photographing based on the detection results on the alignment, the pupil state and the eyelid opening state at the set photographing timing.

Figure 11:
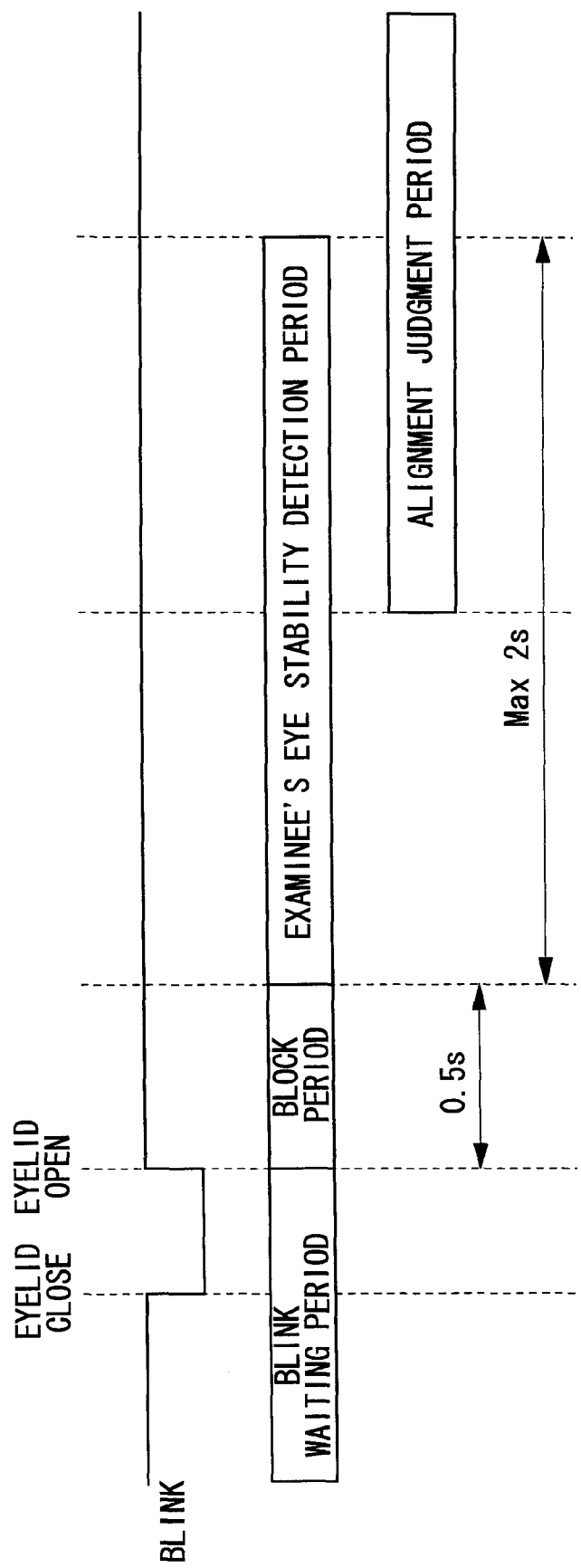
FIG. 11 is a timing chart for illustrating operations after detection of a blink.

When the above conditions are not met and the fixation is judged to be unstable in the predetermined period of time ΔT1 after the detection of the blink, the control unit 80 stops (skips) the detection of the stability of the fixation and shifts to the alignment judgment (see FIG. 11). The control unit 80 once again judges whether or not the alignment conditions, the state of the eyelid, the state of the eyelashes and the pupil diameter are appropriate, and when they are judged to be appropriate, the control unit 80 generates the trigger signal for starting photographing.

When the trigger signal for starting photographing is generated, the control unit 80 drives the inserting/removing mechanism 39 to remove the pop-up mirror 34 from the optical path, drives the inserting/removing mechanism 66 to remove the dichroic mirror 24 from the optical path, and controls the photographing light source 14 to emit light. At the same time, the fundus photographing image is picked up by the image pickup element 35, and image data is stored in the memory 85. Then, the control unit 80 controls the monitor 8 to switch the image displayed thereon to the fundus photographing image in color picked up by the image pickup element 35.

As mentioned above, the control unit 80 suspends the photographing after the automatic photographing mode is brought into the enabled state with the eyelid opening state being appropriate until the closing and opening movements of the eyelid are detected, and uses a detection signal of the closing and opening movements as the trigger signal for starting photographing. As a result, the fundus is photographed in such a state that the tear fluid is spread over the cornea adequately for the photographing, so that a favorable fundus photographing image with less flare can be obtained.

In other words, it is possible to prevent the fundus photographing image from being obtained while being distorted by the tear fluid which is accumulated on the cornea because the eyelid has been open for a long time before the automatic photographing is brought into the enabled state (i.e., resolution degradation, flare and other problems due to tear are prevented). In addition, the possibility of the blink during the photographing can be reduced by performing the photographing after the detection of the blink.

In the case of regarding the detection of the blink of the examinee's eye as the trigger signal for starting photographing as described above, the control unit 80 may give a message for encouraging the examinee to blink. For example, the control unit 80 may control the monitor 8 to display the message for encouraging the examinee to blink (e.g., a message saying that "please slowly blink and widely open your eyes") and make the examiner read the message. A sound generating unit may be provided to the apparatus in order to automatically give the message for encouraging the examinee to blink. In addition, the control unit 80 may control the monitor 8 to display the anterior-segment image between the start of the blink detection and the detection of the blink.

In the above descriptions, the automatic photographing is brought into the enabled state when the predetermined alignment conditions are met, the predetermined focus condition is met, and the state of the eyelid, the state of the eyelashes, and the pupil state are judged to be appropriate. However, the preferred embodiment of the present invention is not limited thereto. The automatic photographing may be brought into the enabled state by input of a predetermined signal. For example, the control unit 80 may bring the automatic photographing into the enabled state based on a detection signal of the alignment state with respect to the examinee's eye and a detection signal of the state of focusing on the fundus.

In the above descriptions, the automatic photographing is brought into the enabled state when a predetermined signal is inputted under the control of the control unit 80, and the photographing timing is automatically set. However, the preferred embodiment of the present invention is applicable to a case where a predetermined signal is manually inputted by the examiner. For example, the control unit 80 may bring the automatic photographing into the enabled state upon input of an operation signal from the photographing switch 4b, automatically set the photographing timing, and perform the automatic photographing using the set photographing timing.

The automatic alignment after bringing the automatic photographing into the enabled state may be configured such that the control unit 80 controls the apparatus main body 3 to be automatically moved and fall within an alignment permissible range which is set narrower than the alignment permissible range before bringing the automatic photographing into the enabled state. When any of the alignment deviation amounts in the X, Y and Z directions falls outside the narrower alignment permissible range, the control unit 80 once again controls the apparatus main body 3 to fall within the narrower alignment permissible range. As a result, it is possible to finely adjust a positional relation between the examinee's eye and the optical axis L1 and obtain a favorable fundus photographing image with less flare.

The control unit 80 may control the monitor 8 to display the targets 100 and 110 on the screen when the automatic photographing mode is selected and control the monitor 8 not to display the targets 100 and 110 on the screen when the manual alignment mode is selected.

The fundus observation screen and the anterior-segment observation screen may be displayed on the same screen. For example, the control unit 80 controls the monitor 8 to display the anterior-segment observation screen (see FIGS. 3 to 4B) in a reduced size when the fundus observation screen (see FIG. 5) is to be displayed, and controls the monitor 8 to display the fundus observation screen (see FIG. 5) in a reduced size when the anterior-segment observation screen (see FIGS. 3 to 4B) is to be displayed. In addition, the photographing may be performed while maintaining the anterior-segment observation screen as shown in FIGS. 3 to 4B, and in such a case, the projection of the focus target may be stopped at the photographing timing as described above, and the fundus observation light source the light from which is slightly visible may be turned off. Thus, the stability of the fixation can be further ensured.

If the control unit 80 judges that the eyelid opening state is not appropriate (error) when the fundus observation screen is displayed, the control unit 80 may switch the fundus observation screen to the anterior-segment screen. Such switching includes enlarging the anterior-segment image from the state of simultaneously displaying the fundus observation image and the anterior-segment image.

A description of an alignment of the apparatus in the working distance direction will be given. The following description will be given on the precondition that the optical axis L1 is positioned at a predetermined reference position of the examinee's eye (e.g., a corneal vertex position or a pupil center position), and the alignment of the apparatus main body 3 with respect to the examinee's eye in the X and Y directions is achieved.

Figure 12A:
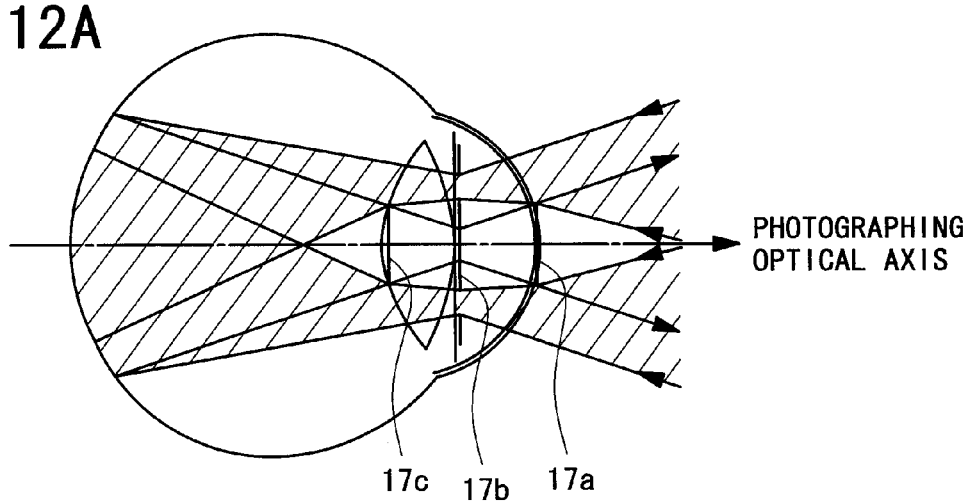
FIG. 12 are views for illustrating a relation between an alignment state in a Z direction and flare.
Figure 12B:
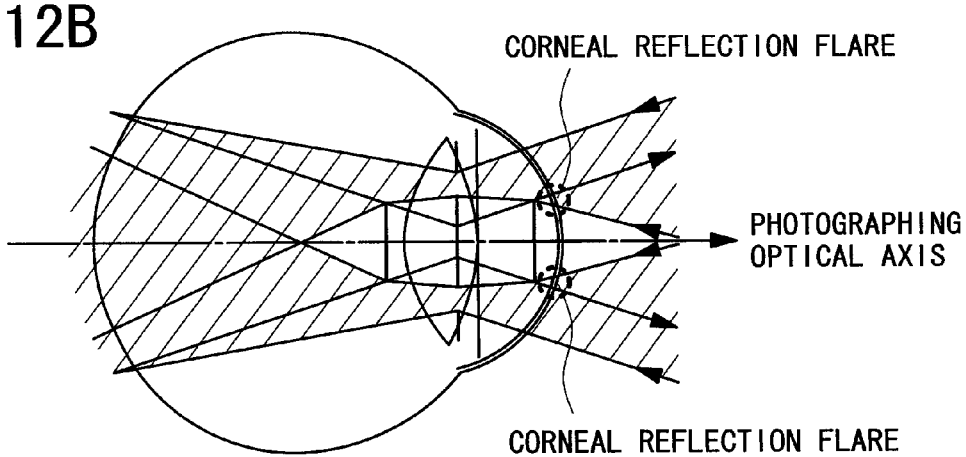
Figure 12C:
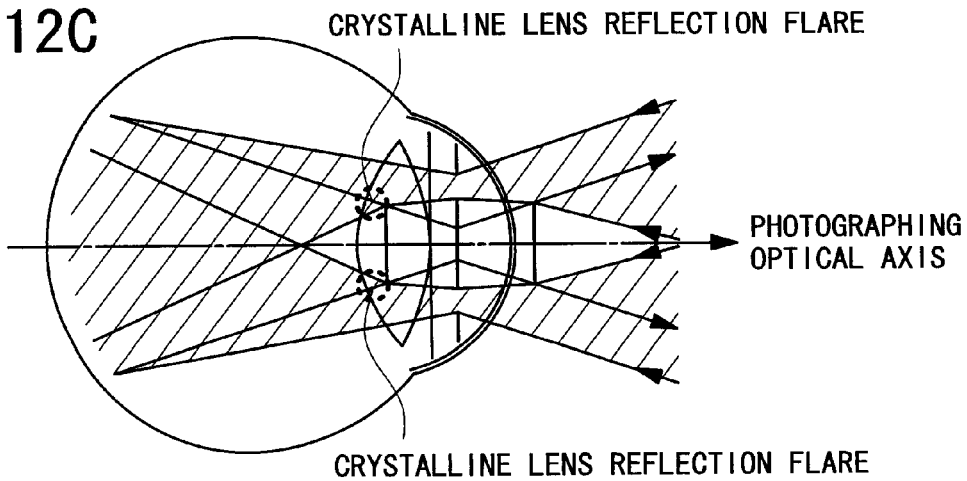

FIGS. 12A to 12C are views showing relations among the first shielding plate 17a, the ring slit 17b, the second shielding plate 17c, and the anterior-segment of the examinee's eye. FIG. 12A is a view showing a case where the ring slit 17b is placed at a position conjugate with the pupil of the examinee's eye. In this case, the cornea and crystalline lens anterior and posterior surfaces of the examinee's eye are out of the common optical path common to the fundus illumination light and the fundus reflection light. Accordingly, the corneal reflection light and the crystalline lens reflection light formed by the fundus illumination light are prevented from being photo-received on the image pickup element 35, which prevents flare in the fundus photographing image.

FIG. 12B is a view showing a case where the apparatus main body 3 is relatively moved closer to the examinee's eye from the alignment reference position. In this case, the cornea of the examinee's eye is positioned on the common optical path common to the fundus illumination light and the fundus reflection light. Accordingly, the corneal reflection light formed by the fundus illumination light is photo-received on the image pickup element 35, causing corneal reflection flare in the fundus photographing image. As the apparatus main body 3 is relatively moved closer to the examinee's eye, the corneal reflection flare is increased.

FIG. 12C is a view showing a case where the apparatus main body 3 is relatively moved away from the examinee's eye from the alignment reference position. In this case, the crystalline lens posterior surface of the examinee's eye is positioned on the common optical path common to the fundus illumination light and the fundus reflection light. Accordingly, crystalline lens posterior surface reflection light formed by the fundus illumination light is photo-received on the image pickup element 35, causing crystalline lens posterior surface reflection flare in the fundus photographing image. As the apparatus main body 3 is moved away from the examinee's eye, the crystalline lens posterior surface reflection flare is increased.

The control unit 80 detects the alignment deviation amount in the Z direction regarding the working distance of the apparatus main body 3 with respect to the examinee's eye in a state where the ring slit 17b is placed at the position conjugate with the pupil of the examinee's eye as a reference working distance (see FIG. 12A). To be specific, the alignment deviation amount in the Z direction is detected using the alignment reference position in the Z direction which is obtained when the ring slit 17b and the pupil of the examinee's eye are conjugate.

The control unit 80 judges that the alignment in the Z direction is appropriate when the alignment deviation amount in the Z direction detected as mentioned above falls within a predetermined alignment permissible range Za. When the alignment deviation amount in the Z direction falls outside the predetermined alignment permissible range Za, the control unit 80 moves the apparatus main body 3 so that the alignment deviation amount in the Z direction falls within the predetermined alignment permissible range Za.

Figure 13:
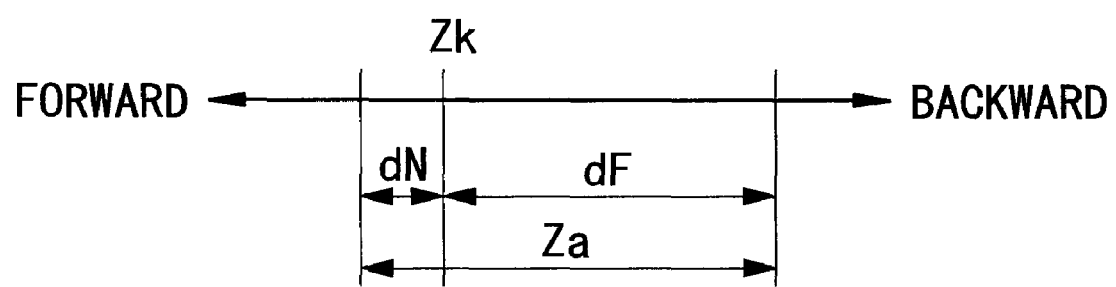
FIG. 13 is a view for illustrating an alignment permissible range Za in the Z direction.

FIG. 13 is a view for illustrating the alignment permissible range Za in the Z direction. The alignment permissible range Za is set to have a narrower range in a direction in which the apparatus main body 3 is relatively moved closer to the examinee's eye with respect to an alignment reference position Zk (including not providing the alignment permissible range), and a wider range in a direction in which the apparatus main body 3 is relatively moved away from the examinee's eye with respect to the alignment reference position Zk. In other words, the alignment permissible range Za is set such that an alignment permissible width dN in the direction in which the apparatus main body 3 is relatively moved closer to the examinee's eye and an alignment permissible width dF in the direction in which the apparatus main body 3 is relatively moved away from the examinee's eye are asymmetrical with respect to the alignment reference position Zk.

By setting the alignment permissible range Za to be wider, the alignment completion condition in the Z direction is relaxed, and the time required for the alignment in the Z direction can be shortened. However, the possibility of causing anterior-segment reflection flare in the fundus photographing image is increased. In contrast, by setting the alignment permissible range Za to be narrower, the alignment completion condition in the Z direction becomes strict, and the anterior-segment reflection flare in the fundus photographing image can be reduced. However, the time required for the alignment in the Z direction is increased.

Hence, according to the preferred embodiment of the present invention, the alignment permissible width dF is made wider to have a relatively high tolerance for the crystalline lens posterior surface reflection flare, and the alignment permissible width dN is made narrower to have a relatively low tolerance for the corneal reflection flare. As a result, the alignment permissible range can be relatively widely ensured, and the alignment can be performed smoothly. In addition, the corneal reflection flare, which is more detrimental to the fundus photographing image than the crystalline lens posterior surface flare, can be prevented, which allows obtaining a favorable fundus photographing image with less flare.

In the above descriptions, the alignment permissible range in the Z direction is configured such that the alignment permissible widths are made asymmetrical with respect to the alignment reference position. However, the preferred embodiment of the present invention is not limited thereto. The alignment permissible range in the X and Y (right/left and up/down) directions may be configured so that the alignment permissible widths are made asymmetrical with respect to the alignment reference position. An example is given on a case where an upper portion of the fundus is photographed with a direction of guiding the fixation of the examinee's eye being guided upward by using a predetermined fixation guiding optical system (e.g., the fixation target presenting optical system 70 shown in FIG. 2). When the alignment reference position in the up/down direction is set such that the corneal vertex of the examinee's eye and the optical axis L1 coincide, the alignment permissible width in a direction of upward movement of the optical axis L1 is made wider, and the alignment permissible width in a direction of downward movement of the optical axis L1 is made narrower. The corneal vertex represents an intersection of a straight line passing through the corneal curvature center of the examinee's eye, which is parallel to the optical axis L1, and the cornea of the examinee's eye.

Figure 6:
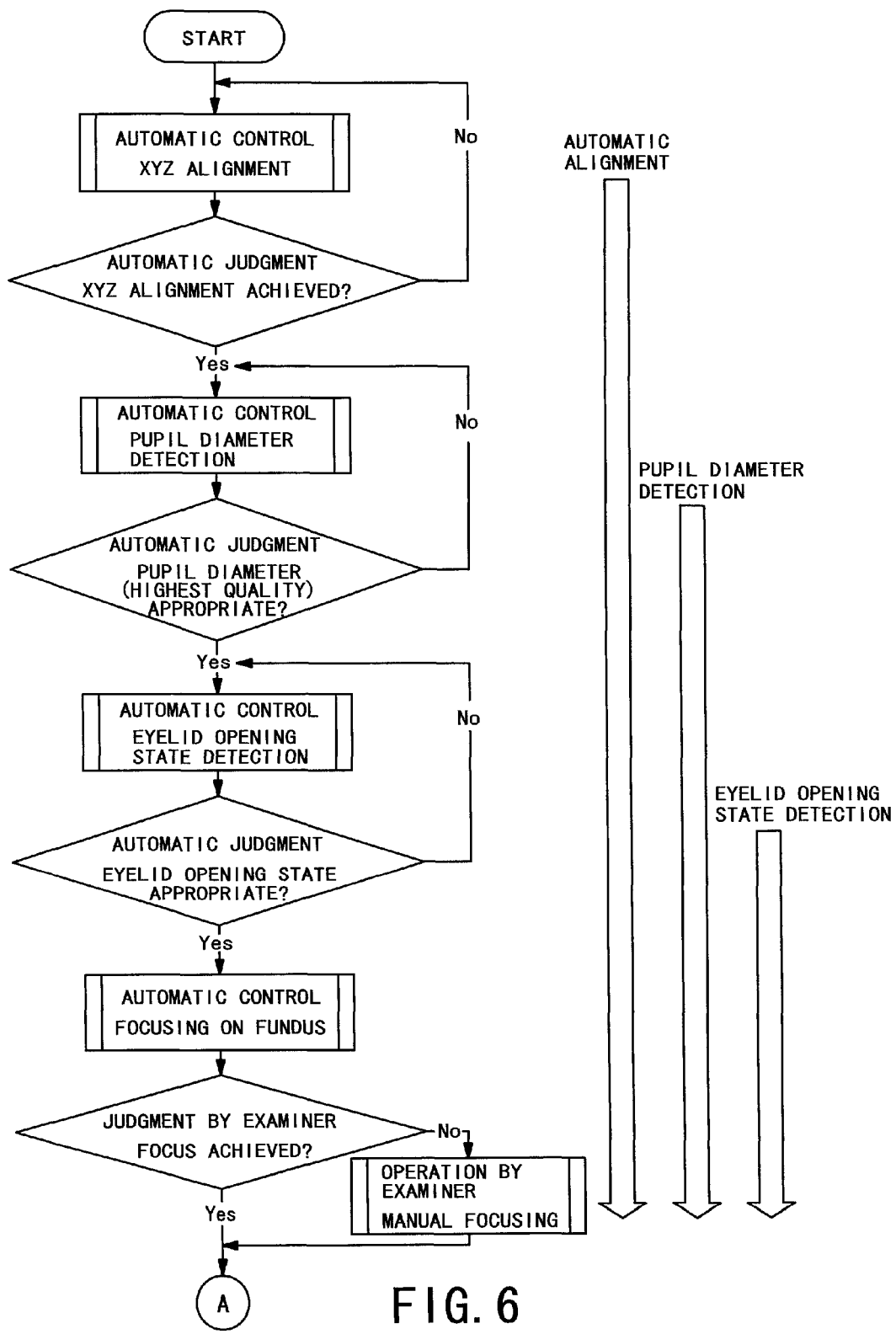
FIG. 6 is a flow chart showing operations of the apparatus.
Figure 14:
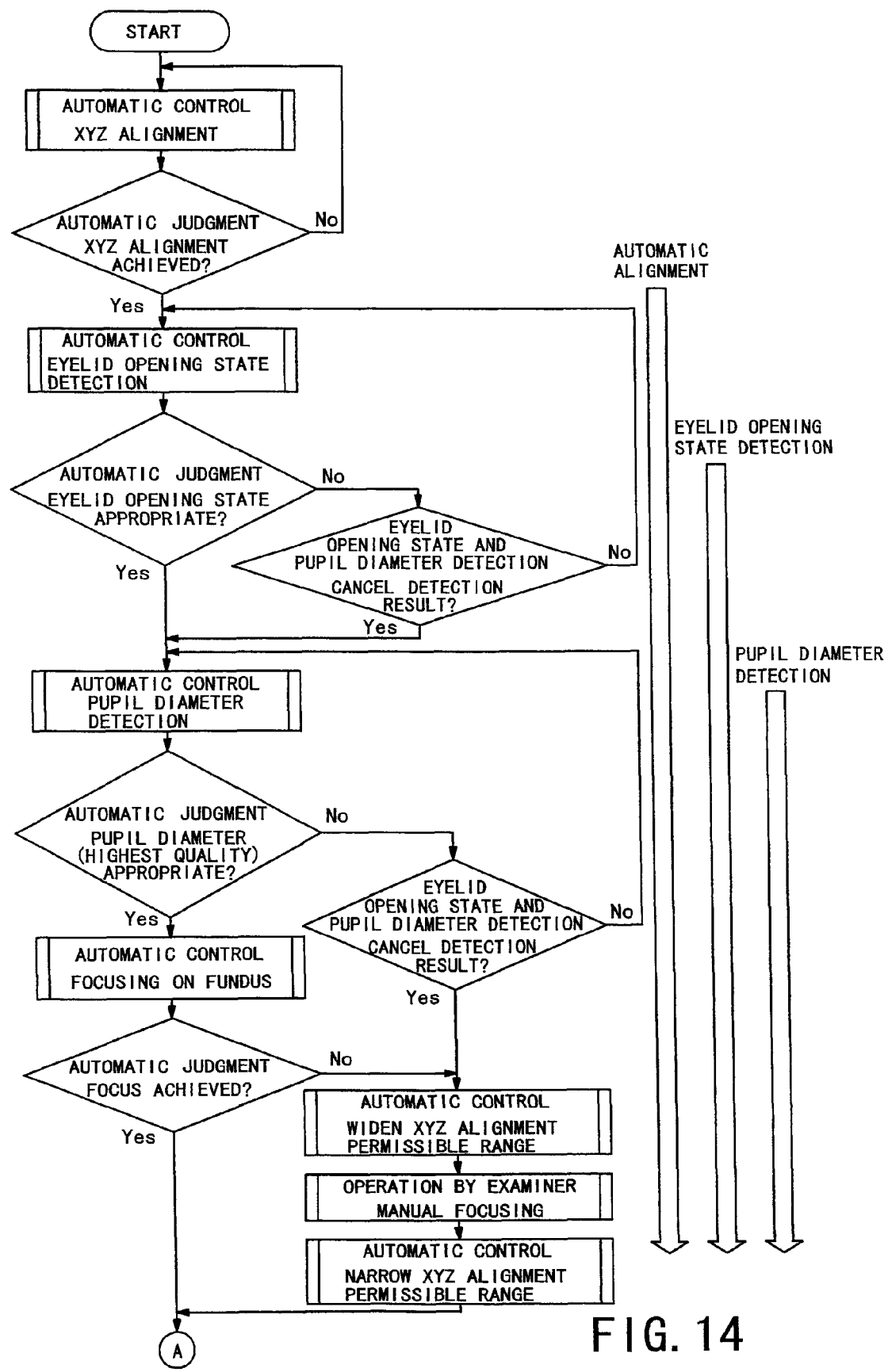
FIG. 14 is a flow chart showing operations of the apparatus when entering a manual focus mode.

FIG. 14 is a flow chart showing the operations of the apparatus when entering the manual focus mode. Detailed descriptions of the same points as the flow chart shown in FIG. 6 are omitted. In FIG. 14, the sequence of the judgment of the eyelid opening state and the judgment of the pupil diameter is altered with respect to FIG. 6.

The control unit 80 performs the automatic alignment with respect to the examinee's eye, the judgment of the eyelid opening state, and the judgment of the pupil diameter, and then performs automatic focus control. Upon completion of the automatic focusing, the control unit 8 controls the monitor 8 to switch to the fundus observation screen. Then, when the automatic photographing is brought into the enabled state, the photographing timing is set taking the detection of the blink of the examinee's eye as a trigger. In FIG. 14, the judgment of the eyelid opening state and the judgment of the pupil diameter may be skipped while cancelling the detection results of the eyelid opening state and the pupil diameter based on an operation signal from a predetermined switch of the switch unit 84. In other words, if the eyelid opening state is judged to be insufficient in the judgment of the eyelid opening state, the predetermined switch is pressed, and the control unit 80 skips the judgment of the eyelid opening state and shifts to the next step.

A projection optical system which projects a target for focusing on the fundus of the examinee's eye (the target projection optical system 40) and a photo-receiving optical system which photo-receives focus target light reflected from the fundus (the fundus observation optical system) are arranged as a focus detection optical system for detecting the state of focusing on the fundus. The state of focusing on the fundus is detected based on a photo-receiving signal outputted from a photodetector in the photo-receiving optical system (the image pickup element 38) to the control unit 80. The control unit 80 drives the moving mechanism 49 in order to focus on the fundus based on a detection signal.

However, in the automatic focus control, if the examinee's eye is microcoria or cataract, the focus target light entering or exiting the examinee's eye is repelled by an iris or an opaque portion of the cataract. Thus, the focus target may not be picked up by the image pickup element 38, preventing the apparatus from executing the automatic focusing.

Therefore, if at least one of the target images S1 and S2 is not detected in the fundus observation image obtained based on the photo-receiving signal from the image pickup element 38 (or when the pupil diameter of the examinee's eye is judged to be insufficient in the pupil diameter judgment before shifting to the automatic focusing, and the pupil diameter judgment is skipped), the control unit 80 generates a judgment signal informing that the automatic focusing is not possible and stops the automatic focus control. Then, the control unit 80 generates a focus mode switching signal for switching from the automatic focus mode to the manual focus mode for performing the manual focusing on the fundus of the examinee's eye. At the same time, the control unit 80 controls the monitor 8 to shift the image displayed thereon to the fundus observation image.

The control unit 80 controls the monitor 8 to give a message indicating the shift to the manual focus mode on the fundus observation screen based on the mode switching signal. In addition, the control unit 80 switches the alignment permissible range in the automatic alignment control from the currently set alignment permissible range A (a first alignment permissible range) to an alignment permissible range B (a second alignment permissible range) which is wider than the alignment permissible range A. When the alignment deviation amount in the X and Y directions detected as described above falls outside the alignment permissible range B, the control unit 80 controls the driving of the XYZ driving unit 6 so that the alignment deviation amount may fall within the alignment permissible range B. Also in the automatic alignment control in the Z direction, the alignment permissible range is preferably switched to a wider alignment permissible range. The alignment permissible range A used in the automatic photographing is preferably a range of plus or minus 0.1 mm with respect to the alignment reference position. In addition, the alignment permissible range B used in the manual focusing is preferably a range of plus or minus 1.5 mm with respect to the alignment reference position.

As a result, the focusing the focus switch 84d is brought into an enabled state. Thus, if at least one of the target images S1 and S2 is displayed on the monitor 8, the examiner operates the focus switch 84d so that the displayed target image is in focus. The control unit 80 drives the moving mechanism 49 based on an operation signal from the focus switch 84d operated by the examiner.

In this case, the automatic alignment is not executed until the alignment deviation amount falls outside the alignment permissible range B. Thus, the examiner relatively moves the apparatus main body 3 with respect to the examinee's eye by means of the joystick 4 and the rotation knob 4b in order that at least one of the target images S1 and S2 may be displayed on the monitor 8. When the apparatus main body 3 is moved in the up/down direction, a part of the focus illumination light to be projected onto the fundus passes through a peripheral portion of the pupil center and at least one of the target images S1 and S2 is displayed on the monitor 8. Thus, the focus switch 84d is operated so that the displayed target image is in focus as mentioned above.

Upon completion of the manual focusing on the fundus as described above, the examiner presses the photographing switch 4b. When the photographing switch 4b is pressed, the operation signal from the photographing switch 4b is outputted as a signal indicating the completion of the manual focusing. Thus, the control unit 80 exits the manual focus mode when the operation signal is outputted from the photographing switch 4b. Then, the control unit 80 switches the alignment permissible range in the automatic alignment control to the alignment permissible range A which is narrower than the alignment permissible range B. Then, the control unit 80 controls the driving of the XYZ driving unit 6 in order that the alignment deviation amount in the X and Y directions may fall within the alignment permissible range A. In such a case, the alignment permissible range in the Z direction is also switched to the narrower alignment permissible range in the automatic alignment control in the Z direction. In other words, the automatic alignment control is restarted with the narrow alignment permissible range.

When the predetermined alignment conditions are met and the eyelid opening state and the pupil state are judged to be appropriate, the control unit 80 brings the automatic photographing into the enabled state and starts the detection of the blink. Then, the control unit 80 sets the timing of the automatic photographing taking the detection of the blink as a trigger, and performs the automatic photographing using the set photographing timing. The subsequent controls are the same as mentioned above, of which descriptions are therefore omitted.

Owing to the configuration as described above, even if the examinee's eye is microcoria or cataract where the automatic focusing is difficult to perform, the manual focusing can be smoothly performed during the process of the automatic photographing of the fundus of the examinee's eye under the automatic alignment control and the automatic focus control. In addition, after the focusing, the automatic alignment control with the strict alignment permissible range and the automatic photographing can be performed by a simple operation, and therefore an inexperienced examiner can easily perform the photographing.

In the above descriptions, the control unit 80 controls the driving of the XYZ driving unit 6 in order that the alignment deviation amount may fall within the alignment permissible range A, and then sets the second alignment permissible range wider than the alignment permissible range A in order to bring the manual focusing into the enabled state. The control unit 80 may suspend the automatic alignment after controlling the driving of the XYZ driving unit 6 in order that the alignment deviation amount may fall within the alignment permissible range A. In such a case, the automatic alignment is restarted when the operation signal is outputted from the photographing switch 4b.

In addition, in the automatic alignment with the alignment permissible range A (the first alignment permissible range) which is performed before entering the manual focus mode and after exiting the manual focus mode, the alignment permissible range A before entering the manual focus mode is not necessarily the same as the alignment permissible range A after exiting the manual focus mode. In other words, it is enough if the alignment permissible range which is narrower than and stricter than the alignment permissible range B is ensured.

The preferred embodiment of the present invention is applicable to the automatic photographing using the manual focusing in which the manual focus mode is initially set by the focus switch 84b. In such a case, after finishing the automatic alignment with respect to the examinee's eye, the judgment of the eyelid opening state and the judgment of the pupil diameter, the control unit 80 stops the automatic alignment control or enlarges the alignment permissible range in order to bring the manual focusing using the focus switch 84d into the enabled state. Then, the control unit 80 exits the manual focus mode based on the operation signal from the photographing switch 4b and restarts the automatic alignment control and the automatic photographing control.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera comprising:
    a photographing optical system for photographing a fundus of an examinee's eye, the photographing optical system comprising
        a visible light source which emits illumination light onto the fundus,
        a focusing lens movable in an optical axis direction thereof, and
        an image pickup element which picks up an image of the fundus;
    a focus detection optical system comprising a first photodetector, for detecting a focus state of the photographing optical system with respect to the fundus;
    a blink sensor which comprises a second photodetector and detects a blink of the examinee's eye based on a photo-receiving signal outputted from the second photodetector; and
    a control unit which is arranged to suspend photographing upon input of a predetermined signal until the blink is detected by the blink sensor, and control the light source to emit the illumination light when a predetermined period of time has passed since the blink is detected by the blink sensor in order to execute the photographing.

2. The fundus camera according to claim 1, further comprising an alignment detection optical system comprising a third photodetector for detecting an alignment state of the photographing optical system with respect to the examinee's eye, wherein
    the control unit is arranged to detect the alignment state based on a photo-receiving signal outputted from the third photodetector, and control the light source to emit the illumination light if the detected alignment state is appropriate when the predetermined period of time has passed since the blink is detected by the blink sensor in order to execute the photographing.

3. The fundus camera according to claim 2, wherein
    the control unit is arranged to detect the focus state based on a photo-receiving signal outputted from the first photodetector, and receive, as the predetermined signal, a signal inputted when the detected alignment state and the detected focus state meet a predetermined alignment condition and a predetermined focus condition, respectively.

4. The fundus camera according to claim 1, further comprising:
    a moving mechanism unit which comprises an electric motor and relatively moves the photographing optical system with respect to the examinee's eye;
    a focus operating member for manual focusing, which is operated by an examiner;
    a lens driving mechanism which moves the focusing lens in the optical axis direction;
    an operation switch arranged to input a signal indicating that the manual focusing is terminated; and
    an alignment detection optical system comprising a third photodetector for detecting an alignment state of the photographing optical system with respect to the examinee's eye, wherein
    the control unit is arranged to detect the alignment state based on a photo-receiving signal outputted from the third photodetector, control driving of the moving mechanism unit based on the detected alignment state in order to execute automatic alignment of the photographing optical system with respect to the examinee's eye with a first alignment permissible range, suspend the automatic alignment or set a second alignment permissible range wider than the first alignment permissible range in order to bring the manual focusing into an enabled state when the alignment state falls within the first alignment permissible range, and control the driving of the moving mechanism unit in order to restart the automatic alignment with the first alignment permissible range when the signal indicating that the manual focusing is terminated is inputted by the operation switch.

5. The fundus camera according to claim 4, wherein
    the control unit is arranged to detect the focus state based on a photo-receiving signal outputted from the first photodetector, control driving of the lens driving mechanism based on the detected focus state in order to perform automatic focusing of the photographing optical system with respect to the fundus, and suspend the automatic alignment or set the second alignment permissible range when a switching signal from the automatic focusing to the manual focusing is generated.

6. The fundus camera according to claim 1, wherein the control unit is arranged to give a message for encouraging the blink of the examinee's eye after the predetermined signal is inputted.

* * * * *